United States Patent [19]

Ohtake et al.

[11] 4,211,704

[45] Jul. 8, 1980

[54] METHOD FOR PRODUCING 2,3,3-TRIMETHYLINDOLENINE

[75] Inventors: Nobumasa Ohtake, Yokohamashi; Ryo Yoshizawa, Yokoshukashi; Isao Koga, Yokohamashi, all of Japan

[73] Assignee: Chisso Corporation, Osaka, Japan

[21] Appl. No.: 930,387

[22] Filed: Aug. 2, 1978

[30] Foreign Application Priority Data

Aug. 29, 1977 [JP] Japan .................................. 52-103381

[51] Int. Cl.$^2$ ............................................. C07D 209/08
[52] U.S. Cl. ................................................... 260/319.1
[58] Field of Search ....................................... 260/319.1

[56] References Cited

U.S. PATENT DOCUMENTS

| 3,905,999 | 9/1975 | Krutak | 260/319.1 |
| 4,062,865 | 12/1977 | Moggi | 260/319.1 |

FOREIGN PATENT DOCUMENTS 50-140440 11/1975 Japan .

OTHER PUBLICATIONS

Sumpter et al., Heterocyclic Compounds with Indole and Carbazole Systems, (Interscience, New York, 1954), pp. 12–15.
Houlihan, ed., Indoles, Part One, (Wiley-Interscience, New York, 1972), pp. 317–319, 324.
Garry et al., Comptes Rendus, vol. 212, pp. 401–404 (1974).

*Primary Examiner*—Alton D. Rollins
*Attorney, Agent, or Firm*—Fred Philpitt

[57] ABSTRACT

A commercial method for producing 2,3,3-trimethylindolenine useful as an intermediate for cationic dyes, etc., with a high yield is provided, which comprises mixing aniline with 3-chloro-3-methylbutane-2-one in a mixing ratio by mol of 3:1–10:1; reacting the resulting mixture at a temperature of 50°–150° C. for 2–20 hours; thereafter elevating the temperature of the reaction liquid; and maintaining the liquid at a reflux temperature of aniline for 0.5–2 hours to complete the reaction.

1 Claim, No Drawings

METHOD FOR PRODUCING 2,3,3-TRIMETHYLINDOLENINE

DESCRIPTION OF THE INVENTION

This invention relates to a method for producing 2,3,3-trimethylindolenine (which will be hereinafter abbreviated to TMI).

TMI is an important synthesis intermediate for cationic dyes and materials for photographic industry. For example, 1,3,3-trimethyl-2-methylene-indoline which is a derivative of TMI and referred to generally as tribase, has been derived from TMI obtained from phenylhydrazine and methyl isopropyl ketone as raw materials according to Fischer's process, or has been prepared by methylating 2,3-dimethylindole obtained from phenylhydrazine and methyl ethyl ketone as raw materials. According to these methods, however, the raw materials are expensive, and moreover since a condensing agent (e.g. zinc chloride, sulfuric acid, hydrochloric acid) is employed at the same time in an amount from an equimolar one to several times this amount, various problems such as corrosion of apparatuses, necessity of treating waste water, etc. occur, and also the operations are troublesome. Thus these methods have had drawbacks in the point of economical and mass production process. Further, Japanese patent application laid-open No. 140440/1975 discloses a synthesis method employing 3-methyl-3-hydroxybutane-2-one as a raw material, but this method has various drawbacks such that the raw material is difficultly available in a cheap cost, and large amounts of water and solvent are used in the reaction system. Thus it is difficult to employ the method as a commerical process.

The present inventors have made various studies for solving these problems, and as a result have found a method for producing TMI economically and with a high yield, by employing as raw materials aniline and, 3-chloro-3-methylbutane-2-one (which will be hereinafter abbreviated to CMBK) capable of being easily prepared from methyl isopropyl ketone according to chlorination. In general, the reaction of α-haloketone with aniline is complicated in the reaction behavior and accompanied with a number of side reactions, whereas the method of the present invention is a commercially advantageous production method having no such drawbacks. Namely the object of the present invention is to provide a commercially advantageous method for producing 2,3,3-trimethylindolenine (TMI) which can be simply practiced without employing a condensing agent, a large amount of water, etc.

The method for producing TMI, of the present invention is characterized by consisting of a former stage of mixing aniline with CMBK in a mixing ratio by mol of 3:1–10:1 and reacting them at a temperature of 50°–150° C. for 2–20 hours, and a latter stage of thereafter elevating the temperature of the resulting reaction mixture and maintaining the mixture at a reflux temperature of aniline for 0.5–2 hours to complete the reaction. It is also possible to carry out the reaction in the presence of aniline hydrochloride salt as a catalyst, if necessary.

The molar ratio of aniline to CMBK in the production method of the present invention is in the range of 3:1–10:1, preferably 5:1–8:1. The reaction temperature is in the range of 50°–150° C., preferably 60°–120° C. The reaction time is in the range of 2–20 hours, preferably 4–20 hours. Further, the specific feature of the present invention is that after the above-mentioned reaction, the temperature of the reaction mixture is elevated and the mixture is maintained at a reflux temperature of aniline for 0.5–2 hours, as mentioned above.

The aniline employed in the present invention is that usually employed and has no particular limitation. Further CMBK can be obtained by chlorinating methyl isopropyl ketone. The molar ratio by mole of aniline hydrochloride salt as catalyst to CMBK is 0.5 or lower, preferably 0.2 or lower.

Further, in the present invention, a solvent can be employed, if necessary. For example, when such a solvent as benzene is employed, it is possible to remove water formed by the reaction to the outside of the system by azeotropy, and as a result, it is possible to reduce the time required for completing the reaction at the latter stage. In the present invention, it is possible to increase the reaction rate by employing a catalyst, to thereby reduce the reaction time. This effectiveness can be exhibited at such a low temperature as 65° C.

According to the method of the present invention, it is possible to obtain 2,3,3-trimethylindolenine (TMI) having a purity of 98.5% with a theoretical yield of 80% to CMBK, and also since it is formed with a good selectivity, the number of components constituting the resulting byproduct and the amount thereof are extremely small. Further, as compared with the conventional methods, there is no problem in respect of apparatus, and since the amount of acidic waste water is notably reduced, there scarcely occur problems concerning the treatment of waste water. Thus the production method of the present invention is advantageous as a commercial mass production method.

Contrary to the present invention, if the former stage reaction is carried out at temperatures higher than 150° C., the resulting byproducts are formed in several kinds and in a large amount from the beginning of the reaction, resulting in a low yield of TMI. Further, since it is difficult to separate the byproducts, a longer time and more operations are required for purifying TMI. If the reaction is carried out at temperatures lower than 50° C., a longer reaction time is required, and hence such a method is unsuitable as a commercial one.

The present invention will be further illustrated by way of the following Examples, but the scope of the present invention is not to be limited thereby.

EXAMPLE 1

233 Gram (2.5 mol) of aniline and 60 g (0.5 mol) of CMBK were fed into a reaction vessel and temperature was elevated to 80° C. at which temperature reaction was carried out for 10 hours. Thereafter the temperature was continuously elevated, and on the way, water formed by condensation, in the form of an azeotropic mixture with aniline was cooled by means of a cooler and withdrawn. The reaction liquid was maintained at a reflux temperature of aniline for one hour to complete the reaction. The liquid was then cooled down to room temperature and treated by sodium hydroxide, followed by separating an oil layer from a water layer. The resulting oil layer was distilled under a reduced pressure (10 mmHg) to obtain 64.6 g of a fraction having a boiling point of 102°–104° C.

The product was subjected to identification by way of infrared spectroscopy and measurement of purity according to gas chromatography (the succeeding Examples and Comparative examples were also subjected to the same identification and measurement of purity), and as a result, it was found to be 2,3,3-trimethylindolenine (TMI) having a purity of 98.5%. The theoretical yield to CMBK was 80%.

EXAMPLE 2

Example 1 was repeated except that 372 g (4.0 mol) of aniline and 60 g (0.5 mol) of CMBK were fed and reaction was carried out at 80° C. for 7 hours. TMI having a purity of 99.0% was obtained. The theoretical yield to CMBK was 81%.

EXAMPLE 3

Example 1 was repeated except that the reaction was carried out at 110° C. for 4 hours. 56.5 Gram of TMI having a purity of 98.5% was obtained. The theoretical yield to CMBK was 70%.

EXAMPLE 4

Example 1 was repeated except that the reaction was carried out at 65° C. for 18 hours. 64 Gram of TMI having a purity of 98.5% was obtained. The theoretical yield to CMBK was 79.3%.

EXAMPLE 5

233 Gram of aniline, 60 g of CMBK and 6.5 g (0.05 mol) of aniline hydrochloride salt were fed into a reaction vessel and reaction was carried out at 80° C. for 7 hours, and the subsequent procedure was carried out in the same manner as in Example 1. 63.7 Gram of TMI having a purity of 98.5% was obtained. The theoretical yield to CMBK was 78.9%.

COMPARATIVE EXAMPLE 1

Example 1 was repeated except that reaction was carried out at 140°–150° C. for 4 hours. 40 Gram of TMI having a purity of 98% was obtained. The theoretical yield to CMBK was 49.3%.

COMPARATIVE EXAMPLE 2

Example 1 was repeated except that reaction was carried out at room temperature for 4 days. As a result of analysis according to gas chromatography, the conversion of CMBK was 41%.

What is claimed is:

1. A method for producing 2,3,3-trimethylindolenine which comprises mixing aniline with 3-chloro-3-methylbutane-2-one in a mol ratio of 3:1–10:1; reacting the resulting mixture at a temperature of 60°–120° C. for 2–20 hours; thereafter elevating the temperature of the reaction liquid; and maintaining the liquid at the reflux temperature of aniline for 0.5–2 hours to complete the reaction.

* * * * *